United States Patent
Matsumoto et al.

(10) Patent No.: US 9,535,013 B2
(45) Date of Patent: Jan. 3, 2017

(54) METHOD AND APPARATUS FOR INSPECTING DEFECT

(75) Inventors: Shunichi Matsumoto, Hitachinaka (JP); Taketo Ueno, Kawasaki (JP); Atsushi Taniguchi, Fujisawa (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 62 days.

(21) Appl. No.: 13/702,696

(22) PCT Filed: May 27, 2011

(86) PCT No.: PCT/JP2011/062188
§ 371 (c)(1),
(2), (4) Date: Jan. 22, 2013

(87) PCT Pub. No.: WO2011/155345
PCT Pub. Date: Dec. 15, 2011

(65) Prior Publication Data
US 2013/0114880 A1    May 9, 2013

(30) Foreign Application Priority Data
Jun. 8, 2010 (JP) ................................. 2010-130910

(51) Int. Cl.
*G01N 21/95* (2006.01)
*G01B 11/30* (2006.01)
(Continued)

(52) U.S. Cl.
CPC ......... *G01N 21/9501* (2013.01); *G01B 11/303* (2013.01); *G01N 21/21* (2013.01); *G01N 21/94* (2013.01); *G01N 21/956* (2013.01)

(58) Field of Classification Search
None
See application file for complete search history.

(56) References Cited

U.S. PATENT DOCUMENTS 4,966,457 A * 10/1990 Hayano .................. G01N 21/94
250/559.41
5,973,814 A * 10/1999 Ohtake ................ G02B 15/173
355/55
(Continued)

FOREIGN PATENT DOCUMENTS

JP       6-97551      4/1994
JP    2000-105203    4/2004
(Continued)

OTHER PUBLICATIONS

Jinendra K. Ranks et al, Visible continuum generation in air-silica microstructure optical fibers with anomalous dispersion at 800 nm, Optics Letters, Jan. 1, 2000, pp. 25-27, vol. 25, No. 1.
(Continued)

*Primary Examiner* — Chan Park
*Assistant Examiner* — Mai Tran
(74) *Attorney, Agent, or Firm* — Baker Botts L.L.P.

(57) ABSTRACT

In inspecting a substrate having a transparent oxide film or a metal film formed on a surface thereof by using a dark field type inspection apparatus installing a laser light source, an illuminating beam having a high coherence causes variations in reflection strength due to multiple interferences within the transparent oxide film or an interference of scattered beams due to the surface roughness of the metal film occurs and which leads to degradation in the sensitivity of defect detection. The present invention solves the problem by providing a low-coherence but high-brightness illumination using a highly directive broadband light source, and a system in which the conventional laser light source is simultaneously employed to selectively use the light sources, thereby enabling a highly sensitive inspection according to the condition of a wafer.

22 Claims, 8 Drawing Sheets

(51) Int. Cl.
*G01N 21/21* (2006.01)
*G01N 21/94* (2006.01)
*G01N 21/956* (2006.01)

(56) References Cited

U.S. PATENT DOCUMENTS

| | | | |
|---|---|---|---|
| 7,492,451 B2* | 2/2009 | Vaez-Iravani | G01N 21/95623 356/237.2 |
| 2001/0048522 A1* | 12/2001 | Yonezawa | G01N 21/88 356/237.2 |
| 2003/0132405 A1* | 7/2003 | Some | G01N 21/95623 250/559.45 |
| 2003/0179369 A1 | 9/2003 | Feldman et al. | |
| 2005/0206887 A1 | 9/2005 | Morioka et al. | |
| 2007/0008455 A1* | 1/2007 | Svec | H04N 5/238 349/62 |
| 2007/0033680 A1* | 2/2007 | Takahashi | G01N 21/9501 359/362 |
| 2007/0077003 A1* | 4/2007 | Aota | G02B 6/2931 385/18 |
| 2008/0024773 A1* | 1/2008 | Miyazaki et al. | 356/237.2 |
| 2008/0144023 A1* | 6/2008 | Shibata | G01N 21/21 356/237.2 |
| 2009/0027664 A1 | 1/2009 | Hamamatsu et al. | |
| 2009/0141269 A1 | 6/2009 | Uto et al. | |
| 2009/0153849 A1* | 6/2009 | Moriya | G01N 21/21 356/239.2 |
| 2009/0279079 A1 | 11/2009 | Shibata et al. | |
| 2010/0106443 A1* | 4/2010 | Shimura et al. | 702/81 |
| 2011/0311132 A1* | 12/2011 | Meimoun | A61B 3/1015 382/162 |

FOREIGN PATENT DOCUMENTS

| | | | |
|---|---|---|---|
| JP | 2005-521065 | 7/2005 | |
| JP | 2007-147475 | 6/2007 | |
| JP | 2007-232555 | 9/2007 | |
| JP | 2007-240512 | 9/2007 | |
| JP | 2009-25221 | 2/2009 | |
| JP | 2009-38339 | 2/2009 | |
| JP | 2009-257903 | 11/2009 | |
| WO | WO03060489 A2 * | 7/2003 | G01N 21/00 |

OTHER PUBLICATIONS

David J. Jones et al., Carrier-Envelope Phase Control of Femtosecond Mode-Locked Lasers and Direct Optical Frequency Synthesis, Science, Apr. 28, 2000, pp. 635-639, vol. 288.

S.H. Moseley et al., Microshutters Arrays for the JWST Near Infrared Spectrograph. SPIE 7010, 2008.

Makoto Mita et al., A MEMS Scanner for 2-dimensinal Scanning LIDAR (Light Detection and Ranging) IEICE Technical Report, (2007-2011), pp. 25-28, vol. 107, No. 365.

* cited by examiner

FIG. 3

| (a) LAYER | (b) PROCESS | (c) MATERIAL | (d) TYPICAL DEFECTS |
|---|---|---|---|
| ELEMENT SEPARATION | DEPOSITION | Si3N4 | FOREIGN PARTICLES |
| | LITHOGRAPHY | RESIST | FOREIGN PARTICLES, PATTERN DEFECTS |
| | ETCHING | Si, Si3N4 | FOREIGN PARTICLES, PATTERN DEFECTS |
| | DEPOSITION | SiO2 | FOREIGN PARTICLES |
| | CMP | Si, SiO2 | FOREIGN PARTICLES, SCRATCHES |
| GATE | DEPOSITION | Poly-Si | FOREIGN PARTICLES |
| | LITHOGRAPHY | RESIST | FOREIGN PARTICLES, PATTERN DEFECTS |
| | ETCHING | Poly-Si | FOREIGN PARTICLES, PATTERN DEFECTS |
| WIRING | DEPOSITION | SiO2 | FOREIGN PARTICLES |
| | LITHOGRAPHY | RESIST | FOREIGN PARTICLES, PATTERN DEFECTS |
| | ETCHING | SiO2 | FOREIGN PARTICLES, PATTERN DEFECTS |
| | DEPOSITION, PLATING | W, Cu | FOREIGN PARTICLES |
| | CMP | SiO2, W, Cu | FOREIGN PARTICLES, SCRATCHES |

FIG. 7A
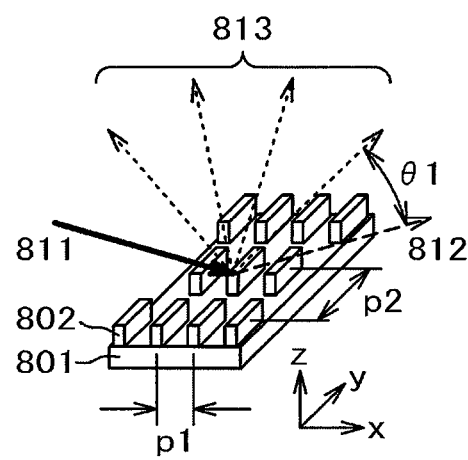
FIG. 7B
(a) : ILLUMINATION OF $\lambda 1$
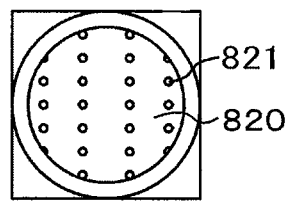
(b)
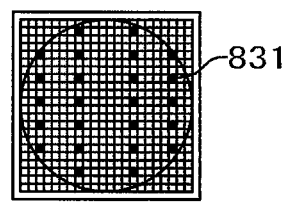
(c) : ILLUMINATION OF $\lambda 1 + \lambda 2$
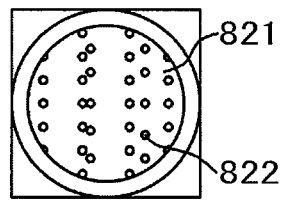
(d)
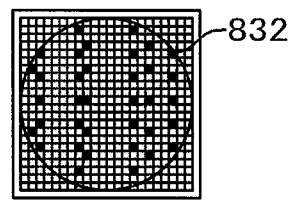
(e) : ILLUMINATION OF $\lambda 1$ to $\lambda 2$
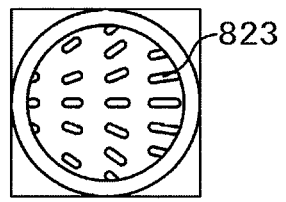
(f)
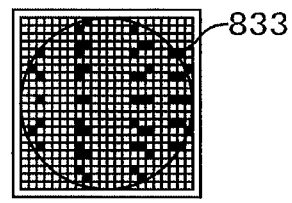
PATTERN DIFFRACTION IMAGE     SETTING OF LIGHT-BLOCKING UNIT

METHOD AND APPARATUS FOR INSPECTING DEFECT

TECHNICAL FIELD

The present invention relates to an inspection technique of detecting defects on an inspection target on the surface of which a pattern is formed on the basis of image information obtained using a light beam, and particularly to an inspection technique of detecting fine defects in which a substrate with a pattern such as a semiconductor wafer is used as an inspection target.

BACKGROUND ART

In a defect inspection for a substrate with a pattern, the sensitivity of defect detection is largely affected depending on how a detected light beam from defects can be detected while being distinguished from a detected light beam (background light noise) from a pattern or a base film. Especially, with advanced fine patterning, detection of finer defects is required in an inspection for a semiconductor wafer, and extracting a weak detected light beam from fine defects while being distinguished from background light noise is a major challenge in an inspection technique.

Here, a vertical structure of a substrate with a pattern as an inspection target and the types of defects to be detected will be described in FIG. 2 using a semiconductor wafer as an example.

In FIG. 2, a vertical structure of a semiconductor device will be described using the reference numerals 20 to 35 and 201 to 251, and defects as inspection targets will be described using the reference numerals 261 to 264.

The reference numeral 20 denotes an element separating layer with a structure (202) in which after digging grooves in a silicon (Si) substrate 201, oxide silicon (SiO2) as an insulating material is embedded to electrically insulate and separate a transistor element formed on a wafer. The reference numerals 21 and 211 denote a gate and contact layer and a gate electrode portion made of polysilicon (poly-Si), respectively. This area largely affects the performance of the transistor, and is important in an inspection. The reference numeral 212 denotes a contact portion formed in such a manner that metal (tungsten: W and the like) is embedded into a hole formed on an insulating film (oxide silicon: SO2) by etching to connect the transistor portion to an upper wiring layer. The reference numerals 22 to 25 denote wiring layers by which circuits are formed. Each layer is embedded with an insulating film (oxide silicon: SiO2 and the like). The reference numeral 22 denotes a first wiring portion in which a first wiring portion 221 is used to be wired in a planar direction and a first via portion 222 is a portion formed in such a manner that metal is embedded into a hole formed on an insulating film (oxide silicon: SiO2 and the like) by etching to be connected to a further-upper wiring layer. Likewise, the reference numeral 23 denotes a second wiring layer in which the reference numerals 231 and 232 denote a second wiring portion and a second via portion, respectively. The reference numeral 24 denotes a third wiring layer in which the reference numerals 241 and 242 denote a third wiring portion and a third via portion, respectively. The reference numeral 25 denotes a fourth wiring layer in which the reference numeral 251 denotes a fourth wiring layer. In each wiring layer, material of the wiring portions is made of metal such as aluminum (Al) or copper (Cu). Further, the metal embedded into the via portions is made of tungsten (W) or copper (Cu).

In addition, defects as inspection targets include scratches 261, short-circuits 262 and disconnections 263 as pattern defects, and foreign particles 264.

FIG. 3 are explanatory diagrams of processes, materials, and typical defects in the respective layers of the semiconductor device shown in FIG. 2. The respective layers of the semiconductor device are formed by a material deposition process for forming each layer, resist pattern formation by a lithography process, an etching process to remove and process the deposited material in accordance with the formed resist pattern, and a CMP (Chemical Mechanical Polishing) process for flattening.

For example, as an apparatus for optically inspecting a semiconductor wafer formed through the respective processes, Patent Literature 1 discloses a technique related to a semiconductor wafer defect inspection apparatus having an illumination system of white light sources in addition to an illumination system of laser light sources.

Further, as a high-coherent broadband light source used for an illumination light source, there is a supercontinuum light source that generates broadband supercontinuum light (SC light) by allowing long and short pulse laser beams to enter a photonic crystal fiber (PCF) in which holes are periodically arranged in the cross-section of the optical fiber as disclosed in Non-patent Literature 1, or an optical frequency comb generator in which electrooptic crystal provided in a resonator is modulated with microwaves by an external transmitter and a single-wavelength laser beam is allowed to enter there to generate light beams with broadband and multi-wavelength spectrums at modulation frequency intervals of microwaves centered on the input single-wavelength laser beam as disclosed in Non-patent Literature 2. Further, as an example of a two-dimensional microshutter array that can be used for a spatial filter of an apparatus for optical inspection, Non-patent Literature 3 and Non-patent Literature 4 disclose a configuration in which thousands to tens of thousands of minute optical shutters having a size to of one to a few hundred of micrometers are arranged and integrated in the X-Y directions using an MEMS (Micro Electro Mechanical Systems) technique, so that each shutter can be individually controlled to be opened or closed.

CITATION LIST

Patent Literature

Patent Document 1: Japanese Patent Application Laid-Open Publication No. 2000-105203

Non-Patent Literature

Non-patent Literature 1: J. K. Ranka, R. S. Windeler, A. J. Stentz, "Visible continuum generation in air-silica microstructure optical fibers with anomalous dispersion at 800 nm", Optical Letter, Vol. 25, No. 1 (2000)

Non-patent Literature 2: J. L. Hall, S. T. Cundiff, "Carrier-envelope phase control of femtosecond mode-locked lasers and direct optical frequency synthesis", Science 288 (2000)

Non-patent Literature 3: S. H. Moseley, "Microshutters Arrays for the JWST Near Infrated Spectrograph", SPIE 7010 (2008)

Non-patent Literature 4: Makoto, MITA, "MEMS scanner for two-dimensional scanning LIDAR": TECHNICAL REPORT OF IEICE, Vol. 107, No. 365 (2007)

SUMMARY OF INVENTION

Technical Problem

There are various types of materials used for each layer of a semiconductor device and each process. In addition, there are many types of defects, as detection targets, such as foreign particles in a deposition process, foreign particles and pattern defects in a lithography process and an etching process for pattern formation, and foreign particles and scratches in a CMP process for polishing.

As described in FIGS. 2 to 3, there are a wide variety of shapes and materials of patterns and defects as detection targets in the inspection for a semiconductor wafer. The inspection apparatus is configured to be able to set plural detection condition parameters so as to optimize the sensitivity of defect detection according to the shapes and materials.

A dark-field optical-type defect inspection apparatus as described in Patent Literature 1 is configured not to collect a specular light beam from the substrate at the objective lens, but to collect a scattered light beam from defects. Further, the light beam collected by the objective lens after being diffracted and scattered from the pattern or base film formed on the substrate is received by the sensor while being suppressed by the polarization filter or the spatial filter. Accordingly, in an inspection image of the dark-field optical-type defect inspection apparatus, defects are exposed as bright spots against a dark background. Thus, if the resolution (the sensor pixel size on the surface of the substrate sample) of the image is rough (up to 1 µm), defects in the order of submicron smaller than the resolution can be detected. Because of this characteristic, the dark-field optical-type defect inspection apparatus is widely used in a production line of semiconductor devices as a high-speed/highly-sensitive inspection apparatus.

On the other hand, the following problems are involved in the dark-field optical-type defect inspection apparatus. One is changes in sensitivity (reduction in sensitivity) of defect detection caused by changes in reflection intensity due to intramembranous multiple interference in an inspection for a wafer on the surface of which an oxide film (transparent film) is formed, and another is reduction in sensitivity of defect detection caused by an increase in background light noise due to interference of scattered light beams resulting from surface roughness (asperities or grains) of a metal film in an inspection for a wafer on the surface of which a metal film is formed. In a manufacturing process of a semiconductor wafer, an inspection is conducted mostly in a state where an oxide film is formed on the surface, a metal film is formed on the surface, or a metal film pattern is formed on an oxide film, as described in FIGS. 2 and 3. In addition, it has been strongly demanded to solve the above-described two problems.

FIG. 4 is a diagram for explaining changes in sensitivity (reduction in sensitivity) of defect detection caused by changes in reflection intensity due to intramembranous multiple interference in an inspection for a wafer on the surface of which an oxide film (transparent film) is formed. In the drawing, the reference numerals 501, 502, and 503 denote an oxide film deposited on a substrate, a defect on the oxide film, and a lower layer of the oxide film, respectively. The reference numeral 511 denotes illumination light beams (laser light beams) that include components 511a that directly illuminate the defect 502 on the oxide film, and components 511b that are reflected by the lower layer 503 after penetrating through the oxide film 501 to illuminate the defect 502. Interference between the two illumination beams corresponds to the amount of light illuminating the defect 502. Further, light beams scattered by the defect 502 include components 512a that directly enter an objective lens 521 to and components 512b that are reflected by the lower layer 503 after penetrating through the oxide film 501 to enter the objective lens. The result of interference between the scattered light components corresponds to the amount of light entering the objective lens.

As described above, the amount of scattered light detected from defects is determined on the basis of the result of interference between illumination light beams and the result of interference between scattered light beams in the defect detection on the oxide film. The amount changes depending on the thickness t of the oxide film 501. The thickness of the oxide film varies depending on the type of semiconductor device. In addition, the design thicknesses of the oxide films are different in the respective layers of the vertical structure described in FIG. 2 even in devices of the same type. Further, the film thickness varies by about ±10% even in the same layer. The changes in the film thickness affect the amount of defect detection light, leading to changes in the sensitivity of defect detection.

FIG. 5 is a diagram for explaining reduction in sensitivity of defect detection caused by an increase in background light noise due to interference of scattered light beams resulting from surface roughness (asperities or grains) of a metal film in an inspection for a wafer on the surface of which a metal film is formed. The reference numeral 601 denotes a metal film; 602, surface roughness; 611, an illumination light beam; 621, an objective lens; 622, an imaging lens; and 623, a sensor. "w" indicates a range where a light beam from the substrate is received by one pixel of the sensor. There are plural concaves and convexes in the range of w, and the result of interference between scattered light beams 612a and 612b determines the amount of light reaching the sensor. If it is assumed that the amplitude of each of the scattered light beams 612a and 612b is A, the intensity of each light beam is A2, and the simple sum of the intensities is A2+A2=2A2. In the case where the light beams are intensified as a result of interference, the intensity of the light is (A+A)2=4A2, and the sensor receives more intensified light beams, resulting in an increase in background light noise. As a result, the sensitivity of defect detection is reduced.

The above-described problems are involved in the dark-field optical-type defect inspection apparatus, and a technique for solving the problems has been demanded. As one means, disclosed is a technique of conducting an inspection with low-coherent broadband illumination (multi-wavelength illumination and white illumination). According to this means, the coherence of illumination light beams can be reduced by illuminating light beams with plural wavelengths at the same time, so that changes in the amount of detected light beam caused by optical interference described in FIGS. 4 and 5 can be reduced. Specifically, changes in reflection intensity caused by intramembranous multiple interference can be reduced for a wafer on the surface of which an oxide film (transparent film) is formed. In addition, background light noise due to surface roughness (asperities or grains) of a metal film can be reduced for a wafer on the surface of which a metal film is formed, and the sensitivity of defect detection for these wafers can be improved.

Patent Literature 1 discloses a technique related to a semiconductor wafer defect inspection apparatus including an illumination system of white light sources in addition to an illumination system of laser light sources. In the method described in Patent Literature 1, it is assumed to use lamps for the white light sources (broadband light sources). In this case, an illumination spot becomes larger in size as compared to that of laser illumination, and thus it is difficult to illuminate light beams with a high degree of brightness. Accordingly, it is necessary to make longer the exposure time (sampling time) of a sensor to obtain the necessary amount of detected light, and the inspection speed is disadvantageously decreased as compared to laser illumination. Further, an illumination system of broadband light sources needs to be additionally provided together with the laser illumination system. Thus, the system of the apparatus becomes disadvantageously complicated.

Solution to Problem

The representative configurations of the present invention to solve the problems are as follows.

Specifically, the present invention provides a defect inspection method including the steps of: selecting a high-coherent broadband light beam with a desired wavelength among those emitted from a high-coherent broadband light source; forming the selected high-coherent broadband light beam with the desired wavelength in a shape long in one direction; obliquely irradiating the selected high-coherent broadband light beam with the desired wavelength formed in the shape long in one direction onto an inspection target on the surface of which a pattern is formed; blocking a scattered light beam from the pattern formed on the inspection target among reflected scattered light beams from the inspection target onto which the selected high-coherent broadband light beam with the desired wavelength formed in the shape long in one direction is obliquely irradiated; capturing an image of a scattered light beam that has not been blocked among the reflected scattered light beams from the inspection target; generating an inspection image from a signal obtained by the captured image; and processing the generated inspection image to extract defects.

Further, the present invention provides a defect inspection apparatus comprising: a broadband light source that emits high-coherent broadband light beams; wavelength selecting unit that selects a high-coherent broadband light beam with a desired wavelength among those emitted from the broadband light source; optical shape forming unit that allows the high-coherent broadband light beam with the desired wavelength selected by the wavelength selecting unit to be formed in a shape long in one direction; irradiation unit that obliquely irradiates the selected high-coherent broadband light beam with the desired wavelength formed in the shape long in one direction by the optical shape forming unit onto an inspection target on the surface of which a pattern is formed; light-collecting unit that collects reflected scattered light beams from the inspection target onto which the selected high-coherent broadband light beam with the desired wavelength formed in the shape long in one direction is obliquely irradiated by the irradiation unit; spatial filter unit that blocks a scattered light beam from a pattern formed on the inspection target among the reflected scattered light beams collected by the light-collecting unit; imaging unit that images an image of a scattered light beam that has not been blocked by the spatial filter unit among the reflected scattered light beams from the inspection target; inspection image generating unit that generates an inspection image from a signal obtained by imaging with the imaging unit; image processing unit that processes the inspection image generated by the inspection image generating unit to extract defects; and control unit that controls the entire apparatus.

Furthermore, the present invention provides a defect inspection apparatus comprising: irradiation unit that obliquely irradiates a light beam onto an inspection target; detection optical unit that blocks a reflected scattered light beam from a pattern formed on the inspection target among those from the inspection target onto which the light beam is irradiated by the irradiation unit, and images an image of a reflected scattered light beam that has not been blocked; and image processing unit that processes the image of the scattered light beam obtained by imaging with the detection optical unit to extract defects of the inspection target, wherein the irradiation unit includes: a broadband light source that emits high-coherent broadband light beams; a wavelength selecting unit that selects a high-coherent broadband light beam with a desired wavelength among those emitted from the broadband light source; an optical shape forming unit that allows the high-coherent broadband light beam with the desired wavelength selected by the wavelength selecting unit to be formed in a shape long in one direction; and irradiation unit that obliquely irradiates the selected high-coherent broadband light beam with the desired wavelength formed in the shape long in one direction by the optical shape forming unit onto the inspection target on the surface of which a pattern is formed.

Advantageous Effects of Invention

According to the aspects of the present invention, the above-described configurations enable to obtain effects in which the sensitivity of defect detection can be improved by reducing interference due to multiple interference of an oxide film and surface roughness of a metal film, the inspection speed same as that of a conventional system using laser illumination can be realized by high-brightness broadband illumination, and the above-described performance can be realized by a simple optical system.

BRIEF DESCRIPTION OF DRAWINGS

FIG. 3(a) is a diagram in which respective layers of the semiconductor device are arranged in the order of manufacturing processes, FIG. 3(b) is a flow diagram for showing a manufacturing process for each layer, FIG. 3(c) shows materials associated with each layer, and FIG. 3(d) is an explanatory diagram of typical defects in the manufacturing process for each layer.

FIG. 7A is an enlarged perspective view of the semiconductor wafer for showing a state in which an illumination light beam hits irregular patterns formed on the semiconductor wafer and scattered light beams are generated from the irregular patterns.

FIG. 7B(a) shows an image of a pupil plane for showing a pattern of scattered light beams formed on the pupil plane of a detection optical system when illuminating a light beam with a single wavelength onto the semiconductor wafer of FIG. 7A, FIG. 7B(b) is a plan view of a light-blocking pattern of the micro-shutter array for light-blocking the pattern of the pupil plane of FIG. 7B (a), FIG. 7B(c) shows an image of the pupil plane for showing a pattern of scattered light beams formed on the pupil plane of the detection optical system when illuminating light beams with two wavelengths onto the semiconductor wafer of FIG. 7A, FIG. 7B(d) is a plan view of a light-blocking pattern of the micro-shutter array for light-blocking the pattern of the pupil plane of FIG. 7B (c), FIG. 7B(e) shows an image of the pupil plane for showing a pattern of scattered light beams formed on the pupil plane of the detection optical system when illuminating a light beam with a certain-width wavelength onto the semiconductor wafer of FIG. 7A, and FIG. 7B(f) is a plan view of a light-blocking pattern of the micro-shutter array for light-blocking the pattern of the pupil plane of FIG. 7B(e).

DESCRIPTION OF EMBODIMENTS

Hereinafter, modes for carrying out the present invention will be described using the drawings.

First Embodiment

An example of applying the present invention to a dark-field illumination-type semiconductor wafer defect inspection apparatus is shown in a first embodiment. A basic configuration of the semiconductor wafer inspection apparatus according to the embodiment will be described on the basis of FIG. 1A.

Figure 1A:
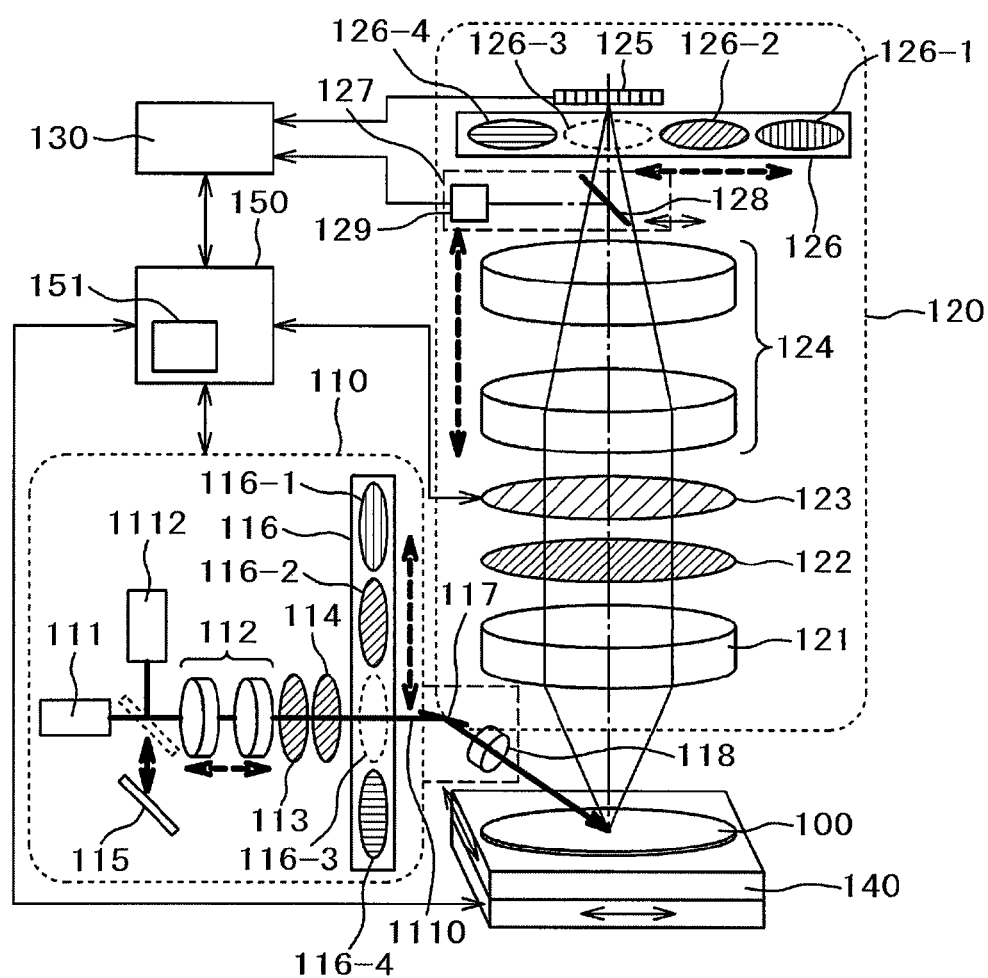
FIG. 1A is a block diagram for showing a basic configuration of a dark-field illumination-type semiconductor wafer defect inspection apparatus in a first embodiment.

The semiconductor wafer inspection apparatus shown in FIG. 1A includes an illumination optical system 110, a detection optical system 120, an image processing unit 130, a stage unit 140 on which a semiconductor wafer (substrate) 100 as a sample is mounted, and a control unit 150 that controls the entire apparatus.

In the illumination optical system 110 of FIG. 1A, the reference numeral 1112 denotes a high-coherent broadband light source. The illumination light source is switched between a laser light source 111 and the high-coherent broadband light source 1112 by a switching mirror 115 in accordance with a target and object of the inspection.

Figure 1B:
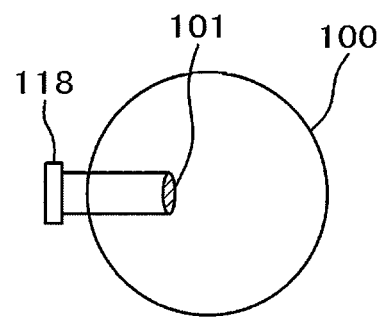
FIG. 1B is a plan view of a semiconductor wafer for showing an illumination area on the semiconductor wafer by an illumination optical system of the dark-field illumination-type semiconductor wafer defect inspection apparatus in the first embodiment.
Figure 2:
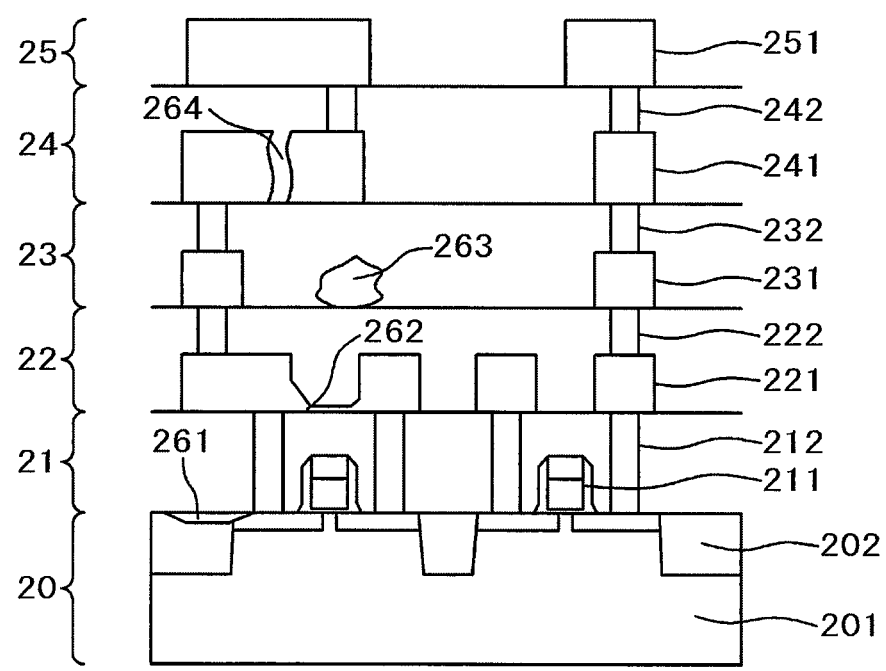
FIG. 2 is a cross-sectional view for showing a vertical structure of a semiconductor device as an inspection target.

The polarization of an illumination light beam 1110 of parallel light fluxes formed in such a manner that a light beam emitted from the light source 111 or 1112 penetrates through a collective lens group 112 is controlled by a polarization control element (wavelength plate or the like) 113, and the amount of illumination light is controlled by a dimming filter 114 to enter a wavelength selecting element unit 116. The illumination light beam with a predetermined wavelength having penetrated through the wavelength selecting element unit 116 is reflected by a mirror 117 so that the optical path is bent, and enters a cylindrical lens 118. Then, while the parallel state of the illumination light beams is kept in one direction by the cylindrical lens 118, the illumination light beam is collected in the other direction (direction orthogonal to the one direction) to illuminate an area 101 long in one direction of the substrate 100 as shown in FIG. 1B.

In this case, as the high-brightness and high-coherent broadband light source 1112, a supercontinuum light source that generates broadband supercontinuum light (SC light) by allowing long and short pulse laser beams to enter a photonic crystal fiber (PCF) in which holes are periodically arranged in the cross-section of the optical fiber can be used as disclosed in Non-patent Literature 1. Alternatively, as disclosed in Non-patent Literature 2, an optical frequency comb generator in which electrooptic crystal provided in a resonator is modulated with microwaves by an external transmitter and a single-wavelength laser beam is allowed to enter there to generate light beams with broadband and multi-wavelength spectrums at modulation frequency intervals of microwaves centered on the input single-wavelength laser beam can be used.

Figure 4:
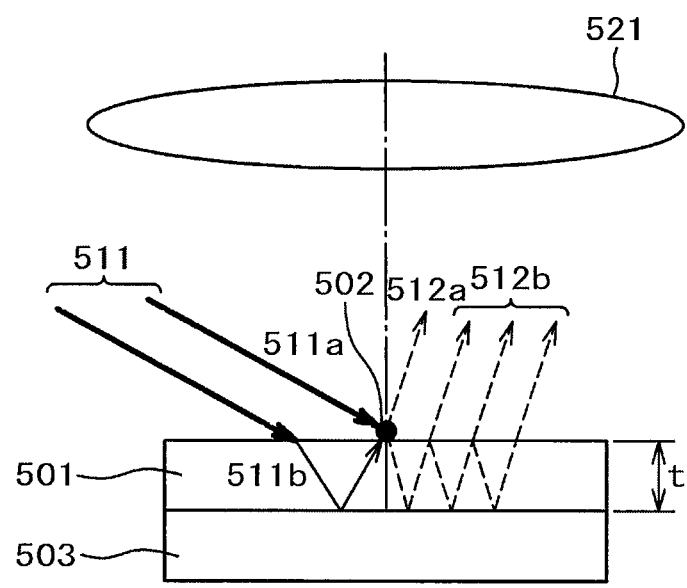
FIG. 4 is a cross-sectional view of the semiconductor wafer and an objective lens for explaining multiple interference caused by an oxide film (transparent film).
Figure 5:
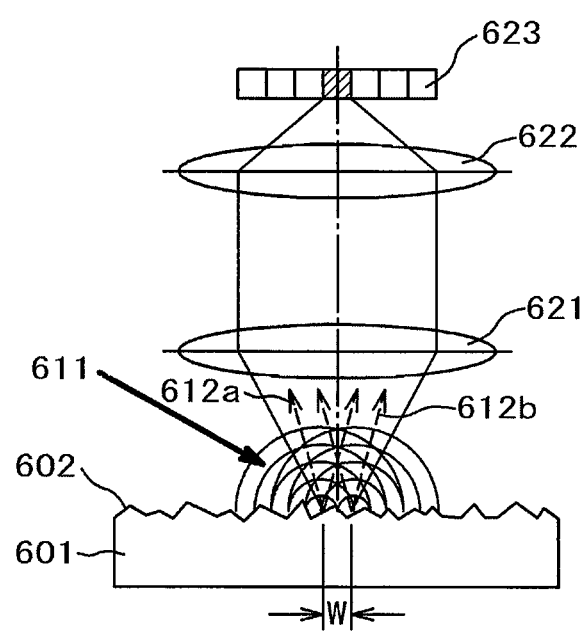
FIG. 5 is a cross-sectional view of a metal film on the semiconductor wafer and a detection optical system for explaining interference of scattered light beams generated due to surface roughness of the metal film.

As described above, the high-brightness and high-coherent broadband light beam is used as an illumination light source, so that the multiple interference of an oxide film and interference due to the surface roughness of a metal film, as described in FIG. 4 and FIG. 5, are reduced to improve the sensitivity of defect detection. In addition, the inspection speed same as that of a laser illumination system can be realized by the high-brightness broadband illumination, and a simple optical system can be realized.

The wavelength selecting element unit 116 selects one of wavelength selecting elements 116-1 to 116-4 to be inserted into the optical path of the illumination light beam. Accordingly, when the broadband light source 1112 is used, only a specific wavelength can be selected for illumination. As settings, the followings are available: (1) use of all wavelengths, (2) use of specific one wavelength, (3) use of specific plural wavelengths, and (4) use of a specific wavelength band. Accordingly, a spatial filter can be used even when the broadband light source 1112 is used (to be described later using FIG. 8). Alternatively, a wavelength with which the sensitivity of defect detection is optimized can be selected based on the fact that optical characteristics (refractive index and absorption coefficient) of material configuring an inspection target are changed depending on wavelengths.

The collective lens group 112 collects the light beams generated from the light source on the inspection target to illuminate the same with a high degree of brightness. In this case, in order to be able to switch the illumination light source or to be able to correct changes in the light-collected position (focal position) due to the above-described wavelength selection, the collective lens group 112 is configured to include plural lens groups and to be provided with a movable mechanism, so that the inspection target can be illuminated with a high degree of brightness irrespective of the light source or the state of wavelength selection.

The reference numeral 120 denotes the detection optical system, and an objective lens 121 collects reflected scattered light beams from defects or patterns existing in the area long in one direction of the semiconductor wafer 100 illuminated by the illumination optical system 110. In a dark-field optical type, no specular light beams from the semiconductor wafer 100 enter the objective lens 121, and light beams scattered by defects are collected as detection light to detect defects. Therefore, the illumination optical system 110 is required to illuminate with a high degree of brightness as described above. The reference numeral 124 denotes imaging lenses by which a detected image of the illuminated area long in one direction of the semiconductor wafer 100 is imaged on a sensor 125. The reference numeral 122 denotes a polarization filter (polarization plate or the like) to filter specific polarization components from the detection light. The reference numeral 123 denotes a spatial filter that blocks regular diffracted light beams generated from patterns that are regularly formed on the semiconductor wafer 100. Thus, background light noise generated at the time of detection can be reduced by the spatial filter to improve the sensitivity of defect detection. The image sensor 125 converts the detected optical image into an electric signal through photoelectric conversion. In general, an array sensor such as a CCD (Charge Coupled Device) sensor or a CMOS (Complementary Metal Oxide Semiconductor) sensor is used.

In the detection optical system 120, the reference numeral 126 denotes a wavelength selecting element unit that includes plural wavelength selecting elements 126-1 to 126-4 as similar to the wavelength selecting element unit 116 in the illumination optical system 110. The wavelength selection, such as (1) use of all wavelengths, (2) use of specific one wavelength, (3) use of specific plural wavelengths, and (4) use of a specific wavelength band, can be made on the detection optical system side.

Further, in order to be able to switch the illumination light source or to be able to correct changes in the imaged position (focal position) due to the above-described wavelength selection, for example, the imaging lenses 124 are configured to include plural lens groups and to be provided with a movable mechanism (not shown) in the detection optical system 120, so that an image of the focused inspection target can be formed on the whole area of the image sensor 125 irrespective of the light source and the state of wavelength selection. Further, the imaging lenses 124 may be provided with a zoom function to control imaging magnifications, so that the sensitivity of defect detection can be optimized.

Furthermore, the detection optical system 120 includes a pupil plane observation optical system 127. When observing a pupil plane, a mirror 128 that is detachable with respect to the optical axis of the detection optical system 120 is arranged on the optical axis of the detection optical system 120 to bend a light beam having penetrated through the imaging lenses 124 towards a monitor camera 129. The monitor camera 129 is arranged at the position conjugate to the pupil plane of the detection optical system 120, and observes the optical pattern of a reflected scattered light beam that is also formed on the spatial filter similarly arranged at the position conjugate to the pupil plane of the detection optical system 120 and is emitted from the pattern formed on the semiconductor wafer 100 onto which the illumination light beam 1110 is irradiated. The mirror 128 is shifted from the optical axis of the detection optical system 120 at the time of inspection to allow the light beam having penetrated through the imaging lenses 124 to reach the image sensor 125.

The image processing unit 130 converts an electric signal output from the image sensor 125 into image data, and detects defects by processing the image data such as comparing the image data with stored reference image data.

The reference numeral 150 denotes the entire control unit that controls the illumination optical system 110, the detection optical system 120, the image processing unit 130, and the stage 140, and includes an input/output unit 151 that inputs processing conditions of the image processing unit 130 or outputs processing results.

The substrate 100 is mounted on the stage 140, and the entire surface of the substrate can be inspected by moving the stage in the X-Y-Z directions.

It should be noted that there has been described a configuration in which the illumination optical system 110 is provided with the wavelength selecting element unit 116 and the detection optical system 120 is provided with the wavelength selecting element unit 126 in the above-described embodiment. However, any one of the wavelength selecting element unit 116 and the wavelength selecting element unit 126 may be provided.

As described above, the dark-field optical-type defect inspection apparatus is configured not to collect a specular light beam from the substrate at the objective lens, but to collect a scattered light beam from defects. Further, the light beam collected by the objective lens after being diffracted and scattered from the pattern or base film formed on the substrate is received by the sensor while being suppressed by the polarization filter or the spatial filter. Accordingly, in an inspection image of the dark-field optical-type defect inspection apparatus, defects are exposed as bright spots against a dark background. Thus, if the resolution (the sensor pixel size on the surface of the substrate sample) of the image is rough (up to 1 μm), defects in the order of submicron smaller than the resolution can be detected. Because of this characteristic, the dark-field optical-type defect inspection apparatus is widely used in a production line of semiconductor devices as a high-speed/highly-sensitive inspection apparatus.

FIG. 6 are explanatory diagrams of a two-dimensional microshutter array used for the spatial filter 123. The microshutter array is formed in such a manner that thousands to tens of thousands of minute optical shutters having a size of one to a few hundred of micrometers are arranged and integrated in the X-Y directions using an MEMS (Micro Electro Mechanical Systems) technique as disclosed in Non-patent Literature 3 and Non-patent Literature 4, so that each shutter can be individually controlled to be opened or closed.

Figure 6A:
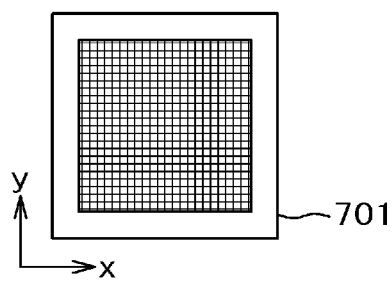
FIG. 6A is a plan view of a micro-shutter array.

The reference numeral 701 of FIG. 6A denotes the entire two-dimensional microshutter array. Each grid serves as an optical shutter.

Figure 6B:
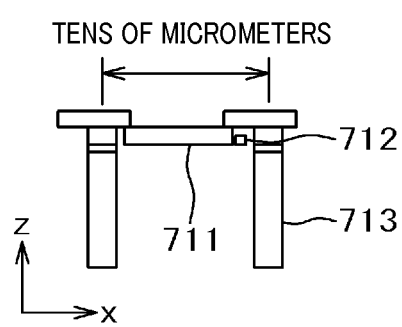
FIG. 6B is a cross-sectional view of an optical shutter for showing a state in which one optical shutter of the micro-shutter array is closed.
Figure 6C:
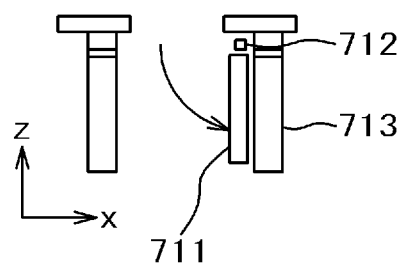
FIG. 6C is a cross-sectional view of the optical shutter for showing a state in which one optical shutter of the micro-shutter array is opened.

FIGS. 6B and 6C are diagrams for explaining opening and closing states of one optical shutter, in which FIG. 6B shows a closing state of the shutter and FIG. 6C shows an opening state of the shutter. In each drawing, the reference numerals 711, 712, and 713 denote a shutter body, a torsion bar for supporting the shutter, and a structure to keep the strength of the shutter array, respectively. As shown in FIG. 6B, the shutter is usually closed by the spring force of the torsion bar. Electromagnetic force or electrostatic force is generated at the structure 713 to attract the shutter 711 to the structure 713, so that the shutter is opened as shown in FIG. 6C.

FIG. 7A shows an example of patterns formed on the surface of the inspection target and is a diagram for explaining diffracted light beams generated from the patterns. On the surface of an inspection target 801, arranged are patterns 802 at pitches p1 in the X direction and at pitches p2 in the Y direction. As the pitch θ of the diffraction angle of a diffracted light beam when an illumination light beam 811 with a wavelength λ is irradiated onto the surface, sin θ1 is equal to λ/p1 in the X direction and sin θ2 (not shown) is equal to λ/p2 in the y direction.

FIG. 7B are diagrams each explaining a light-blocking state by the two-dimensional microshutter array. FIG. 7B are diagrams each explaining an image of the diffracted light beam at the spatial filter position (the pupil position of the detection optical system) of the detection optical system and a light-blocking state by the two-dimensional microshutter array. FIG. 7B(a) shows a case of laser illumination or illumination by selecting specific one wavelength (λ1) from the broadband light source with the wavelength selecting means. The reference numerals 820 and 821 denote the pupil of the detection optical system 120 and a diffraction image, respectively. The diffraction images are generated at equal intervals in the X-Y directions corresponding to the pitches represented by the above-described equations. In response to this, the light-blocking position of the two-dimensional microshutter array is shown by the reference numeral 831 as illustrated in FIG. 7B(b). The light-blocking position of the two-dimensional microshutter array is determined in such a manner that the pupil plane of the detection optical system 120 is imaged by the camera 129 of the pupil plane observation optical system 127 to detect the optical pattern (FIG. 7B(a)) of the reflected scattered light beam from the semiconductor wafer 100 in the pupil plane. Specifically, the two-dimensional microshutter array at the position corresponding to the detected optical pattern is driven by the entire control unit 150, so that the light-blocking pattern of the two-dimensional microshutter array as shown in FIG. 7B(b) can be formed.

FIG. 7B(c) shows a case of illumination by selecting specific two wavelengths (λ1 and λ2) from the broadband light source with the wavelength selecting means, and diffraction images 821 and 822 at different pitches corresponding to the respective wavelengths are generated. In response to this, the light-blocking position of the two-dimensional microshutter array is shown by the reference numeral 832 as illustrated in FIG. 7B(d). Further, FIG. 7B(e) shows a case of illumination by selecting a specific wavelength band (λ1 to λ2) from the broadband light source with the wavelength selecting means, and a diffraction image 823 corresponding to the wavelength band illuminated is generated. In response to this, the light-blocking position of the two-dimensional microshutter array is shown by the reference numeral 833 as illustrated in FIG. 7B(f).

As described above, even when a wavelength is selected using broadband illumination for a light source, the spatial filter can be allowed to effectively function by using the two-dimensional microshutter array for the spatial filter, and the sensitivity of defect detection can be improved.

As in the embodiment, an inspection is conducted using a light source of low-coherent broadband illumination (multi-wavelength illumination and white illumination), so that the coherence of the illumination light beams can be reduced by illuminating light beams with plural wavelengths at the same time, changes in the amount of detected light beam caused by optical interference can be reduced, and changes in reflection intensity by intramembranous multiple interference can be reduced. Further, even for a wafer on the surface of which a metal film is formed, background light noise caused by the surface roughness (asperities or grains) of the metal film can be reduced by the two-dimensional microshutter array, and the sensitivity of defect detection for the wafer can be improved.

Second Embodiment

Figure 8:
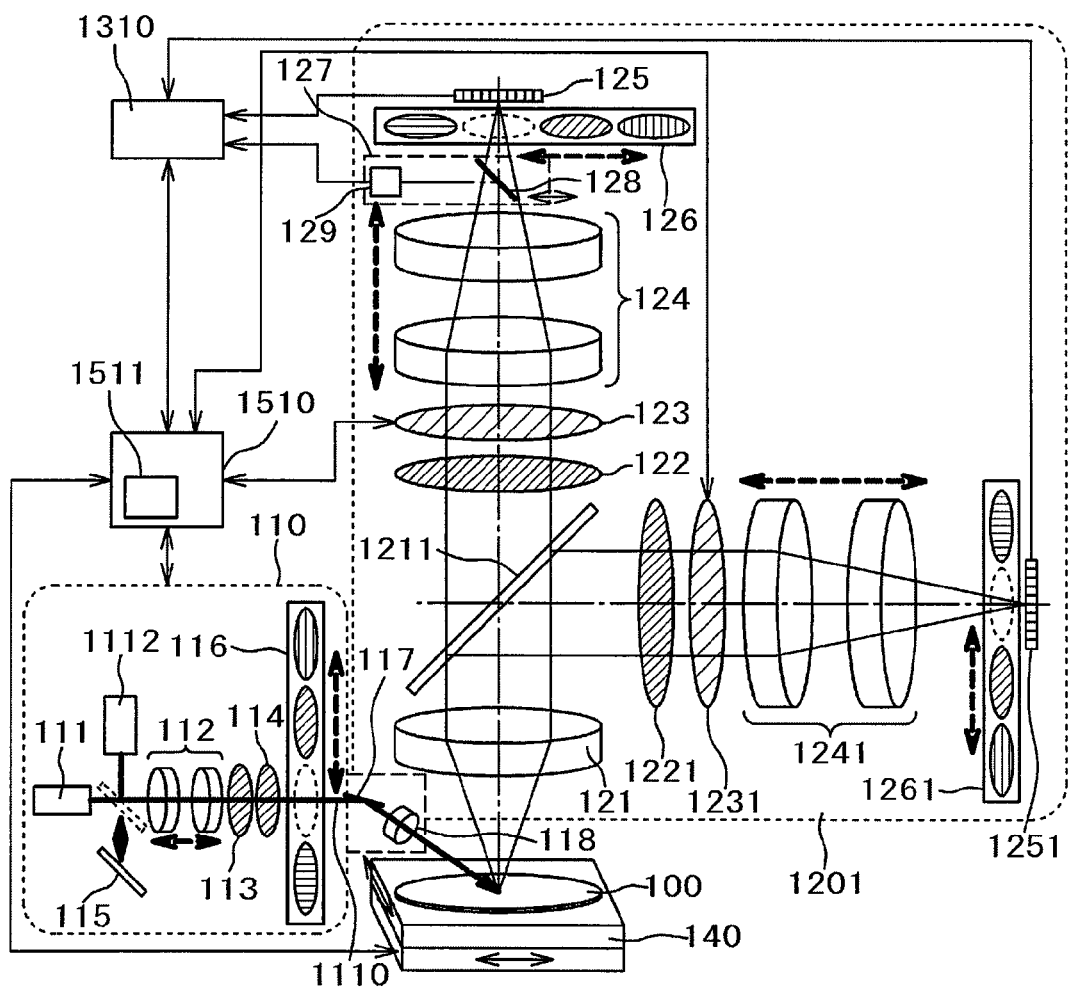
FIG. 8 is a block diagram for showing a basic configuration of a dark-field illumination-type semiconductor wafer defect inspection apparatus in a second embodiment.

FIG. 8 is an explanatory diagram of a second embodiment of the present invention.

In addition to the configuration of the first embodiment of the present invention described using FIG. 1, an optical path branch mechanism 1211 (half mirror or the like) is provided on the objective lens 121 of a detection optical system 1201 in FIG. 8. While a first detection system includes optical systems 122 to 126 as similar to the case of the first embodiment, a second detection system branched at the optical path branch mechanism 1211 includes second optical filtering means (a polarization filter 1221, a spatial filter 1231, and a wavelength selecting element unit 1261), a second imaging lens 1241, and a second image sensor 1251. Further, the second optical filtering means of the second detection system can be controlled independently from the first optical filtering means (the polarization filter 122, the spatial filter 123, and the wavelength selecting element unit 126) of the first detection system.

It should be noted that the spatial filter 1231 of the second detection system is provided at the pupil plane of the second detection system.

In this configuration, the patterns of the pupil plane appearing at the positions of the spatial filter 123 and the spatial filter 1231 have the same shape. Thus, the pupil plane observation optical system 127 is provided in the first detection system as similar to the first embodiment, and the spatial filters 123 and 1231 are controlled by an entire control unit 1510 on the basis of the image of the pupil plane of the first detection system observed by the pupil plane observation optical system 127 to form the light-blocking pattern of the two-dimensional shutter array for each filter.

Accordingly, two inspection images can be obtained at the same time by two image sensors 125 and 1251 under different optical conditions (for example, wavelength selecting elements with different characteristics are set in the wavelength selecting element unit 126 and the wavelength selecting element 1261 to select different wavelengths, or different polarization conditions are set in the polarization filter 122 and the polarization filter 1221). The two inspection images are processed by an image processing unit 1310, so that defects can be determined on the basis of the amount of information greater than image processing with a single image, and the sensitivity of detection can be improved.

Third Embodiment

Figure 9:
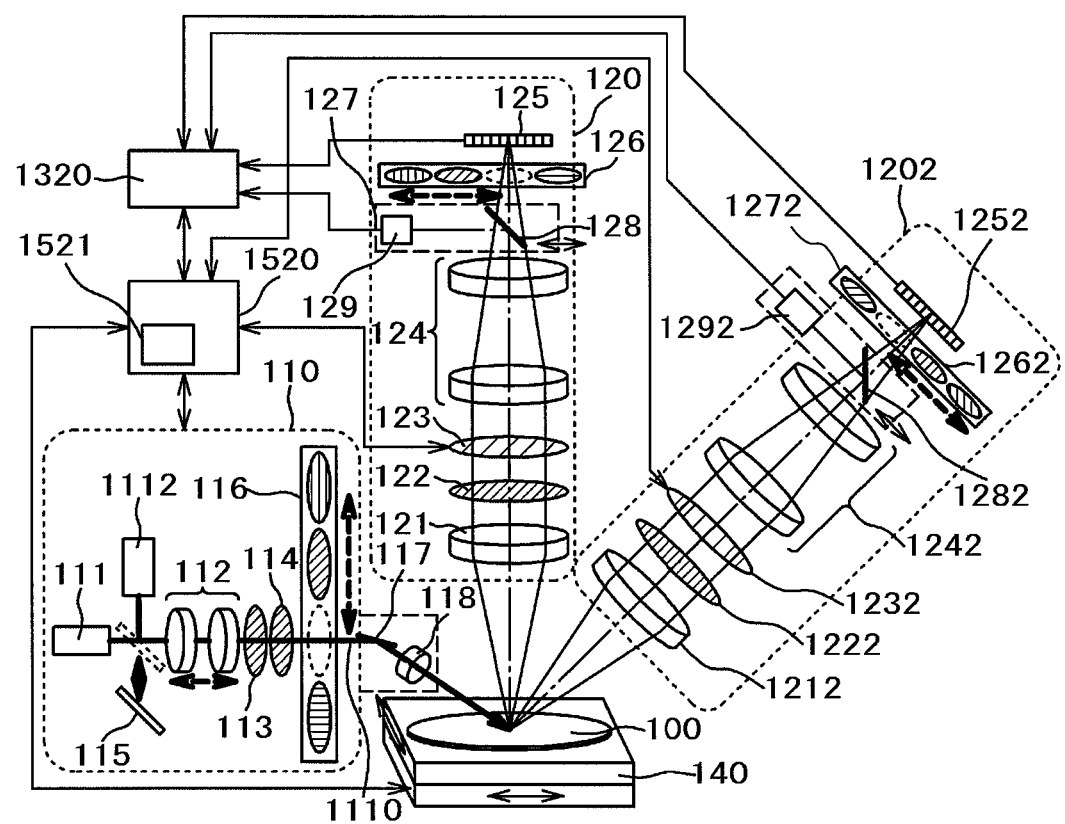
FIG. 9 is a block diagram for showing a basic configuration of a dark-field illumination-type semiconductor wafer defect inspection apparatus in a third embodiment.

FIG. 9 is a diagram for showing a configuration of a semiconductor wafer inspection apparatus in a third embodiment of the present invention. In the embodiment, in addition to the configuration of the semiconductor wafer inspection apparatus described using FIG. 1 in the first embodiment, a second detection optical system 1202, namely, a second objective lens 1212, second optical filtering means (a polarization filter 1222, a spatial filter 1232, and a wavelength selecting element 1262), a second imaging lens 1242, and a second image sensor 1252 are provided. The configuration and function of the illumination optical system 110 are the same as those described in the first embodiment.

As similar to the second embodiment, the second optical filtering means can be controlled independently from the first optical filtering means (the polarization filter 122, the spatial filter 123, and the wavelength selecting element 126) of the first detection optical system 120.

In this configuration, the patterns of the pupil plane appearing at the positions of the spatial filter 123 and the spatial filter 1232 are different in the shape from each other. Thus, the first pupil plane observation optical system 127 is provided in the first detection system, and a second pupil plane observation optical system 1272 is provided in the second detection system. The spatial filter 123 is controlled by an entire control unit 1520 on the basis of an image of the pupil plane of the first detection system observed by imaging, using the monitor camera 129, a reflected scattered light beam from the semiconductor wafer 100 bent by the mirror 128 of the pupil plane observation optical system 127 inserted in the optical path of the first detection system 120. On the other hand, the spatial filter 1232 is controlled by the entire control unit 1520 on the basis of an image of the pupil plane of the second detection system observed by imaging, using a monitor camera 1292, a reflected scattered light beam from the semiconductor wafer 100 bent by a mirror 1282 of the pupil plane observation optical system 1272 inserted in the optical path of the second detection system 1202. Accordingly, the light-blocking pattern of the two-dimensional shutter array is formed for each of the spatial filter 123 and the spatial filter 1232.

Accordingly, two inspection images can be obtained at the same time by two image sensors 125 and 1252 under different optical conditions. The two inspection images are processed by an image processing unit 1320, so that defects can be determined on the basis of the amount of information greater than image processing with a single image, and the sensitivity of detection can be improved.

It should be noted that the optical axis of the first detection optical system is orthogonal to the surface of the inspection target and the optical axis of the second detection optical system is inclined relative to the orthogonal direction of the surface of the inspection target in FIG. 9. However, the present invention is not limited to this arrangement, but the optical axis may be inclined relative to the orthogonal direction of the surface of the inspection target in each of the first and second detection optical systems.

Further, there has been described a configuration in which the illumination optical system 110 includes the laser light source 111 and the broadband light source 1112 to select one of the light sources using the switching mirror 115 in the above-described first to third embodiments. However, the present invention is not limited to this configuration, but only the broadband light source 1112 may be provided without using the laser light source 111 and the switching mirror 115.

In the above description, an inspection for a semiconductor wafer has been described as an example. However, the present invention is not limited to the above embodiments, but may be applied to an inspection method and an inspection apparatus for an inspection target on which patterns are formed. For example, the present invention can be applied to an inspection for substrates of flat panel displays (liquid crystal displays, plasma displays, organic EL displays, and the like) and storage products (DTM: discrete track media and BPM: bit pattern media) on which patterns are formed.

INDUSTRIAL APPLICABILITY

While a substrate with a pattern such as a semiconductor wafer is used as an inspection target, the present invention can be used for an inspection apparatus that detects defects on the inspection target on the surface of which a pattern is formed on the basis of image information obtained using light beams.

REFERENCE SIGNS LIST

100 . . . semiconductor wafer 110 . . . illumination optical system 111 . . . laser light source 1112 . . . high-coherent broadband light source 112 . . . collective optical system 113 . . . polarization control element 114 . . . dimming element 116 . . . wavelength selecting element unit 120 . . . detection optical system 121 . . . objective lens 122 . . . polarization filter 123 . . . spatial filter 124 . . . imaging lens 125 . . . image sensor 126 . . . wavelength selecting element unit 127 . . . pupil plane observation optical system 130 . . . image processing unit 140 . . . stage 150 . . . entire control unit

The invention claimed is:

1. A defect inspection method, including the steps of:
   emitting high-coherent broadband light beams from a high-coherent broadband light source;
   collecting the high-coherent broadband light beams emitted from the high-coherent broadband light source with a collective lens group configured to include plural lens groups provided with a first movable mechanism;
   selecting a wavelength condition from wavelength conditions of using at least one desired wavelength and of using a desired wavelength band in the high-coherent broadband light beams emitted from the high-coherent broadband light source collected by the collective lens group;
   selecting a high-coherent broadband light beam with the selected wavelength condition among those emitted from the high-coherent broadband light source;
   forming the high-coherent broadband light beam with the selected wavelength condition in a shape long in one direction;
   obliquely irradiating the high-coherent broadband light beam with the desired selected wavelength condition formed in the shape long in one direction onto an inspection target on the surface of which a pattern is formed;
   blocking a scattered light beam from the pattern formed on the inspection target by using a spatial filter among reflected scattered light beams from the inspection target onto which the high-coherent broadband light beam with the selected wavelength condition formed in the shape long in one direction is obliquely irradiated;
   capturing an image of a scattered light beam that has not been blocked among the reflected scattered light beams from the inspection target and passed through imaging lenses configured to include plural lens groups whose focal position is adjustable to the selected wavelength condition by using a second movable mechanism;
   generating an inspection image from a signal obtained by the capturing; and
   processing the generated inspection image to extract defects wherein the first movable mechanism, the second movable mechanism, and the spatial filter are controlled according to the selected wavelength.

2. The defect inspection method according to claim 1, wherein in the step of capturing an image, an image of a scattered light beam having penetrated through a wavelength selecting filter among those that have not been blocked among the reflected scattered light beams from the inspection target is captured, wherein in the step of generating, an inspection image is generated from a signal obtained by the capturing, and wherein in the step of processing, the generated inspection image is processed to extract defects.

3. The defect inspection method according to claim 1, wherein in the step of selecting, the high-coherent broadband light beam with the selected wavelength condition is selected after the high-coherent broadband light beam emitted from the high-coherent broadband light source is polarized in a desired polarization state by a polarization filter.

4. The defect inspection method according to claim 1, wherein in the step of blocking, the scattered light beam from the pattern formed on the inspection target among the reflected scattered light beams from the inspection target is blocked by a spatial filter of a two-dimensionally-arranged microshutter array.

5. The defect inspection method according to claim 4, wherein in the step of blocking, an image of the reflected scattered light beam from the inspection target at the position where the two-dimensionally-arranged microshutter array is arranged is monitored, and a light-blocking pattern of the spatial filter that blocks the reflected scattered light beam with the two-dimensionally-arranged microshutter array is generated using information of the monitored image of the reflected scattered light beam.

6. The defect inspection method according to claim 1, wherein in the step of selecting, the high-coherent broadband light beam with the selected wavelength condition is selected among those emitted from the high-coherent broadband light source by using a wavelength selecting filter selected from a plurality of wavelength selecting filters corresponding to the selected wavelength condition.

7. A defect inspection apparatus, comprising:
a high-coherent broadband light source that emits high-coherent broadband light beams;
a collective lens group configured to include plural lens groups to collect the high-coherent broadband light beams emitted from the high-coherent broadband light source;
a first movable mechanism which moves at least one lens among the plural lens groups configuring the collective lens group;
a selecting circuit configured to select a wavelength condition from wavelength conditions of using at least one desired wavelength and using a desired wavelength band in the high-coherent broadband light beams emitted from the high-coherent broadband light source:
a wavelength selecting mechanism select a high-coherent broadband light beam with the selected wavelength among those emitted from the high-coherent broadband light source and collected by the collective lens group;
an optical shape forming mechanism allow the high-coherent broadband light beam with the desired wavelength condition selected by the wavelength selecting mechanism to be formed in a shape long in one direction;
an irradiation device configured to obliquely irradiate the high-coherent broadband light beam with the selected wavelength condition formed in the shape long in one direction by the optical shape forming mechanism onto an inspection target on the surface of which a pattern is formed;
a light-collecting lens group having a plurality of lenses configured to collect reflected scattered light beams from the inspection target onto which the selected high-coherent broadband light beam with the selected wavelength condition formed in the shape long in one direction by the irradiation unit is obliquely irradiated;

a second movable mechanism which moves at least one lens among the plurality of lenses of the light-collecting lens group;
a spatial filter that blocks a scattered light beam from a pattern formed on the inspection target among the reflected scattered light beams collected by the light-collecting lens;
an imaging lens configured to image an image of a scattered light beam that has not been blocked by the spatial filter among the reflected scattered light beams from the inspection target and configured to include plural lens groups whose focal position is adjustable to the selected wavelength condition;
an inspection image generating circuit configured to generate an inspection image from a signal obtained by imaging with the imaging unit;
an image processor configured to process the inspection image generated by the inspection image generator to extract defects; and
a control unit which controls over all the defect inspection apparatus, wherein the control unit controls the first movable mechanism, the second movable mechanism, and the spatial filter according to the selected wavelength condition.

8. The defect inspection apparatus according to claim 7, further comprising a polarization filter configured to polarize the high-coherent broadband light beams emitted from the high-coherent broadband light source in a desired polarization state, wherein the high-coherent broadband light beam with a selected wavelength condition is selected by the wavelength selecting mechanism among those polarized in the desired polarization state by the polarization filter.

9. The defect inspection apparatus according to claim 7, wherein
the spatial filter further comprises a two-dimensionally-arranged microshutter array, and a scattered light beam from a pattern formed on the inspection target among the reflected scattered light beams from the inspection target is blocked by the two-dimensionally-arranged microshutter array.

10. The defect inspection apparatus according to claim 9, further comprising a monitor configured to monitor an image of the reflected scattered light beams from the inspection target, wherein
the control configured to control the two-dimensionally-arranged microshutter array to generate a light-blocking pattern of the spatial filter that blocks the reflected scattered light beam using information of an image of the reflected scattered light beam obtained by imaging with the monitor an image of the reflected scattered light beam from the inspection target at the position where the two-dimensionally-arranged microshutter array is arranged.

11. The defect inspection apparatus according to claim 7, wherein
the wavelength selecting mechanism includes a plurality of wavelength selecting filters, and the high-coherent broadband light beam with the selected wavelength condition is selected among those by using a wavelength selecting filter selected from the plurality of wavelength selecting filters corresponding to the selected wavelength condition.

12. The defect inspection apparatus according to claim 7, further comprising a laser light source and optical path switch, wherein
when the laser light source is selected by the optical path switch, a laser beam emitted from the laser light source is irradiated onto the inspection target through the optical shape former and the irradiation element.

13. A defect inspection apparatus comprising:
an irradiation device that includes a high-coherent broadband light source configured to emit high-coherent broadband light beams and to obliquely irradiate a light beam onto an inspection target;
a collective lens group configured to include plural lens groups to collect the high-coherent broadband light beams emitted from the high-coherent broadband light source;
a first movable mechanism which moves at least one lens among lenses comprising the collective lens group;
a second movable mechanism which moves at least one lens among lenses comprising the collective lens group;
a selecting circuit configured to select a wavelength condition from wavelength conditions of using at least one desired wavelength and using a desired wavelength band in the high-coherent broadband light beams emitted from the high-coherent broadband light source;
a control unit which controls the first movable mechanism, the second movable mechanism, and a spatial filter according to the selected wavelength condition;
an optical detector configured to block reflected scattered light beam from a pattern formed on the inspection target among those from the inspection target onto which the light beam is irradiated by the irradiation unit, and images an image of a reflected scattered light beam that has not been blocked and passed through imaging lenses configured to include plural lens groups whose focal position is adjustable to the selected wavelength condition; and
an image processor configured to process the image of the scattered light beam obtained by imaging with the optical detector to extract defects of the inspection target, wherein the irradiation device includes a wavelength selector to select a high-coherent broadband light beam with the selected wavelength condition among those emitted from the high-coherent broadband light source and collected by the collective lens group, and
an optical shape forming mechanism configured to allow the high-coherent broadband light beam with the selected wavelength condition selected by the wavelength selecting mechanism to be formed in a shape long in one direction, said irradiation device being configured to obliquely irradiate the selected high-coherent broadband light beam with the desired wavelength formed in the shape long in one direction by the optical shape forming mechanism onto the inspection target on the surface of which a pattern is formed.

14. The defect inspection apparatus according to claim 13, further comprising a polarization filter configured to polarize the high-coherent broadband light beam emitted from the broadband light source in a desired polarization state, wherein
the high-coherent broadband light beam with the selected wavelength condition is selected by the wavelength selector among those polarized in the desired polarization state by the polarization filter.

15. The defect inspection apparatus according to claim 13, wherein
the optical detector includes a spatial filter having a two-dimensionally-arranged microshutter array, and a reflected scattered light beam from a pattern formed on the inspection target is blocked by the two-dimensionally-arranged microshutter array.

16. The defect inspection apparatus according to claim 15, further comprising a monitor configured to monitor an image of the reflected scattered light beams from the inspection target
wherein
the control circuit is configured to control the two-dimensionally-arranged microshutter array to generate a light-blocking pattern of the spatial filter that blocks the reflected scattered light beam using information of an image of the reflected scattered light beam obtained by imaging with the monitor unit an image of the reflected scattered light beam from the inspection target at the position where the two-dimensionally-arranged microshutter array is arranged.

17. The defect inspection method according to claim 1, wherein in the step of blocking, the scattered light beam from the pattern formed on the inspection target among the reflected scattered light beams from the inspection target is blocked by a spatial filter having a light blocking pattern which is adjustable by the selected wavelength of the high-coherent broadband light beam.

18. The defect inspection method according to claim 1, wherein in the step of emitting, the high-coherent broadband light beams are emitted from a supercontinuum light source.

19. The defect inspection apparatus according to claim 7, wherein the spatial filter having a light blocking pattern which is adjustable by the selected wavelength of the high-coherent broadband light beam.

20. The defect inspection apparatus according to claim 7, wherein the high-coherent broadband light source is a supercontinuum light source.

21. The defect inspection apparatus according to claim 13, wherein the optical detector includes a spatial filter having a light blocking pattern which is adjustable by the selected wavelength of the high-coherent broadband light beam.

22. The defect inspection apparatus according to claim 13, wherein the high-coherent broadband light source of the irradiation device is a supercontinuum light source.

* * * * *